United States Patent [19]

van Paassen

[11] Patent Number: 4,759,931

[45] Date of Patent: Jul. 26, 1988

[54] NOVEL LIQUID IODOPHORS

[75] Inventor: Nicolaas A. I. van Paassen, Bodegraven, Netherlands

[73] Assignee: 501 Stamicarbon B.V., Geleen, Netherlands

[21] Appl. No.: 598,809

[22] Filed: Apr. 10, 1984

[30] Foreign Application Priority Data

Apr. 20, 1983 [NL] Netherlands ................... 8301389

[51] Int. Cl.$^4$ .................. A01N 59/12; C11D 3/48; C07C 59/48; C07C 59/10
[52] U.S. Cl. .................................. 424/150; 252/106; 562/471; 562/587
[58] Field of Search ................. 424/150; 252/106; 562/471, 587

[56] References Cited

U.S. PATENT DOCUMENTS

| Re. 29,909 | 2/1979 | Kurtz ................................. 424/150 |
| 2,210,874 | 8/1940 | Balle ................................. 562/471 |
| 2,931,777 | 5/1960 | Shelanski ......................... 424/150 |
| 2,989,434 | 6/1961 | Brost et al. ...................... 424/150 |
| 3,438,907 | 4/1969 | Schmolka ......................... 424/150 |
| 3,983,171 | 9/1976 | Vanlerberghe et al. ......... 562/471 |

FOREIGN PATENT DOCUMENTS

| 1097069 | 1/1961 | Fed. Rep. of Germany ...... 562/471 |
| 283986 | 6/1952 | Switzerland ..................... 562/471 |
| 926898 | 5/1963 | United Kingdom .............. 562/471 |
| 1027481 | 4/1966 | United Kingdom .............. 562/587 |
| 2088863 | 6/1982 | United Kingdom .............. 562/587 |
| 721298 | 1/1985 | United Kingdom .............. 252/106 |

Primary Examiner—Albert T. Meyers
Assistant Examiner—John M. Kilcoyne
Attorney, Agent, or Firm—Ladas & Parry

[57] ABSTRACT

Liquid iodophors are provided containing as surface-active agent a product of the formula RO—$(C_3H_6O)_m$—$(C_2H_4O)_n$—$CH_2COOM$, wherein RO is the residue of an alcohol of at least 8 carbon atoms or of an alkylphenol of at least 10 carbon atoms which is substantially free of olefinic unsaturation, m is a number having an average value of 0–10, n is a number having an average value of 2–20 and M is hydrogen or a monovalent cation. Preferably the iodophors contain at least 20% of iodine. The novel iodophors are prepared by dissolving at room temperature the desired amount of iodine in the surface-active agent.

2 Claims, No Drawings

NOVEL LIQUID IODOPHORS

This invention relates to novel iodophors. By iodophors are understood products, wherein surface-active agents act as carriers and solubilizing agents for iodine, vide the Merck Index, 9th edition, 1976, page 665.

Previously the non-ionic surface-active agents were considered the most suitable surface-active agents for this purpose. Thus, in an article starting on page 61 of Soap & Chemical Specialities, 43, No. 8 (1967) only non-ionic detergents are mentioned by name, and also the book "Desinfection, Sterilization and Preservation" by C. A. Lawrence and S. S. Block (1971) on pages 334 and 335 and the work by N. Schönfeldt, "Grenzflächenaktive Aethylenoxid-Addukte" (1976) on page 708 mention a clear preference for the non-ionic surface-active agents over the ionic ones. This preference is particularly based on the fact that the non-ionic agents are stable over a broad pH range. According to the last-mentioned literature reference up to 30% iodine can be brought into solution.

It has been found that compounds of the class of the ethercarboxylic acids always can bring into solution large to very large amounts of iodine and that—and this is an important advantage—this is always possible at room temperature. Of course, the hydrophobic residues of these ethercarboxylic acids should satisfy two additional conditions. Firstly, since the object of the invention is the preparation of liquid iodophors the ethercarboxylic acids should not be solids thus compounds with, for instance, stearyl residues generally will not enter into consideration in practice. Secondly, the surface-active compound should not contain any important degree of olefinic unsaturation, because otherwise the iodine would react therewith. Accordingly, compounds with, for instance, an oleyl residue should be present at most in small amounts and preferably should be completely absent.

Accordingly, the invention relates to liquid iodophors, wherein the surface-active agent is a product of the formula $RO-(C_3H_6O)_m-(C_2H_4O)_n-CH_2COOM$, wherein RO is the residue of an alcohol of at least 8 carbon atoms or of an alkylphenol of at least 10 carbon atoms which is practically free of olefinic unsaturation, m is a number having an average value of 0–10, n is a number having an average of 2–20 and M is hydrogen or a monovalent cation.

The ethercarboxylic acids are weak acids and consequently in their free acid form they are the most closely related to the non-ionic surface-active agents which are usually used for iodophors. However, it appears surprisingly that they can take up more iodine in the entirely or partially neutralized form, wherein they are accordingly more ionic in nature.

Another surprising aspect is that the influence of the number of oxyethylene units with an identical hydrophobic residue is small. Accordingly, there is obviously no simple connection between HLB value and take-up capacity for iodine.

The ethercarboxylic acids derived from aliphatic alcohols generally can dissolve even larger amounts of iodine than the ethercarboxylic acids derived from alkylphenols. However, also with these latter compounds one can dissolve without heating for instance 20% of iodine, which is a suitable amount for actual practice.

As has been mentioned previously, liquid iodophors are involved. Solid ethercarboxylic acids are not suitable according to the invention, because the iodine can dissolve therein only with heating and on cooling solid products are obtained again. Therefore, ethercarboxylic acids derived from cetyl or stearyl alcohol do not enter into consideration.

Particularly suitable are ethercarboxylic acids derived from natural alcohols of vegetable origin, such as mixtures of lauryl and myristyl alcohol. In actual practice such natural alcohol mixtures often contain also small amounts of higher and unsaturated alcohols which accordingly also will turn up in the ethercarboxylic acids. However, such small amounts do not interfere in practice, even though a small amount of unsaturation also means a small iodine loss.

Throughout the following examples, which are given for illustrative purposes only and which do not serve to limit the scope of the invention in any way, the oxyethylene groups will always be rendered with "EO" and oxypropylene groups with "PO". The alcohol residue derived from lauryl alcohol obtained from vegetable material (about 70% of lauryl alcohol and about 30% of myristyl alcohol) is indicated hereinbelow as $L_{70}M_{30}$, and OF and NF mean octylphenyl and nonylphenyl, respectively.

EXAMPLE 1

It was tried to dissolve 20% of iodine in the following three ethercarboxylic acids:
(a) $L_{70}M_{30}O(EO)_{4.5}-CH_2COONa$
(b) $L_{70}M_{30}O(EO)_{10}-CH_2COONa$
(c) $NFO(EO)_{15}-CH_2COONa$ In all three cases the 20% of iodine could be dissolved without heating. Only the nonylphenyl derivative required a somewhat longer dissolving time.

EXAMPLE 2

This example shows the effect of neutralization of the free carboxylic acid. Starting products were $L_{70}M_{30}O(EO)_{4.5}-CH_2COOH$ and $L_{70}M_{30}O(EO)_{10}-CH_2COOH$. For both products the maximum amount of iodine was determined which could be dissolved therein without heating, whereafter both products were neutralized first about halfway to the sodium salt (pH about 4) and then completely (pH about 6), and in both cases again the maximum amount of iodine was determined which could be dissolved without heating. The results are as follows:

| $L_{70}M_{30}O(EO)_{4.5}-CH_2COOH$ | % dissolved iodine | $L_{70}M_{30}O(EO)_{10}-CH_2COOH$ | % dissolved iodine |
|---|---|---|---|
| Not neutralized | 16.7 | Not neutralized | 16.7 |
| Half neutralized | 42.9 | Half neutralized | 42.1 |
| Completely neutralized | 54.5 | Completely neutralized | 54.4 |

EXAMPLE 3

An attempt was made to dissolve 20% of iodine without heating in a number of related, non-ionic surface-active products, i.e. the following:

(a) NFO(EO)$_{9.5}$H
(b) NFO(EO)$_4$H
(c) OFO(EO)$_4$H
(d) OFO(EO)$_{10}$H
(e) myristyl—O—(EO)$_2$H (narrow cut, prepared with SbCl$_5$ as the catalyst)
(f) myristyl—O—(EO)$_5$H In none of these cases was it possible to dissolve the 20% of iodine. Thereafter a further experiment was carried out as compound f, wherein the material was molten; hereby indeed a solution was formed having the desired iodine content.

For comparison a solution with 20% iodine was prepared without heating with the following ethercarboxylic acids:
(g) mixture of 93.1% by weight of OF—O—(EO)$_6$—CH$_6$COOH plus 6.9% by weight of 50% NaOH
(h) 93.9% by weight of NF—O—(EO)$_7$—CH$_2$COOH plus 6.1% by weight of 50% NaOH
(i) 92.9% by weight of NF—O—(EO)$_4$—CH$_2$COOH plus 7.1% by weight of 50% NaOH
(j) 91.9% by weight of myristyl—O—(EO)$_{3.5}$—CH$_2$COOH plus 8.1% by weight of 50% NaOH
The ethoxylation in that case had been carried out again with SbCl$_5$ so that the product possessed a narrow distribution of the number of EO-units.
(k) 92.9% by weight of myristyl—O—(EO)$_6$—CH$_2$COOH plus 7.1% by weight of 50% NaOH
(l) 92.5% by weight of decyl—O—(EO)$_8$—CH$_2$COOH plus 7.5% by weight of 50% NaOH

EXAMPLE 4

The product myristyl—O—(EO)$_6$—CH$_2$COOH was tested in partially neutralized form (92.9% by weight of this ethercarboxylic acid with 7.1% by weight of 50% NaOH) for the possibility to incorporate therein without heating 30%, 40% and 50% iodine. It appeared that both 40% and 30% of iodine dissolved in this product at room temperature within 15 minutes. With an amount of 50% of iodine solid pieces were still in the mixture after half an hour. It appears therefrom that the solubility limit for iodine in this half neutralized product is in any case over 40%.

EXAMPLE 5

The following ethercarboxylic acids were used:
(a) 93% by weight of OFO(PO)$_4$(EO)$_2$—CH$_2$COOH
(b) 93% by weight of L$_{70}$M$_{30}$O(PO)(EO)$_5$—CH$_2$COOH
(c) 93% by weight of decyl—O—(PO)$_2$(EO)$_3$—CH$_2$COOH Each of these ethercarboxylic acids was neutralized with 50% NaOH to pH 4. In these three partially neutralized ethercarboxylic acids iodine wad dissolved at room temperature to a content of 20%. This appeared possible in all three cases, although this took some more time than is the case with the ethercarboxylic acids without propyleneoxide residues. The obtained solutions were well stable.

What is claimed is:

1. A liquid iodophor, consisting essentially of a surface-active agent of the formula RO—(C$_3$H$_6$O)$_m$—(C$_2$H$_4$O)$_n$—CH$_2$COOM, wherein RO is the residue of an alcohol of at least 8 carbon atoms or an alkylphenol of at least 10 carbon atoms which is substantially free of olefinic unsaturation, m is a number from 0–10, n is a number from 2–20 and M represents hydrogen or a monovalent cation, and iodine, and said surface active agent being in the neutralized or partially neutralized form, said iodophor containing at least 20% of iodine.

2. A process for preparing a liquid iodophor comprising neutralizing or partially neutralizing a surface-active agent of the formula RO—(C$_3$H$_6$O)$_m$—(C$_2$H$_4$O)$_n$—CH$_2$COOM, wherein RO is the residue of an alcohol of at least 8 carbon atoms or an alkylphenol of at least 10 carbon atoms which is substantially free of olefinic unsaturation, m is a number from 0–10, n is a number from 2–20 and M represents hydrogen or a monovalent cation, and dissolving at least 20% of iodine at room temperature in said surface-active agent.

* * * * *